United States Patent [19]

Vassiliadis

[11] Patent Number: 4,491,131

[45] Date of Patent: Jan. 1, 1985

[54] LASER DEVICE FOR GYNECOLOGY

[75] Inventor: Arthur Vassiliadis, Colorado Springs, Colo.

[73] Assignee: Xanar, Inc., Colorado Springs, Colo.

[21] Appl. No.: 371,329

[22] Filed: Apr. 23, 1982

[51] Int. Cl.³ .............................................. A61B 17/36
[52] U.S. Cl. .................................. 128/303.1; 128/395
[58] Field of Search .................... 128/303.1, 395–398; 219/121 L, 121 LV, 121 LR

[56] References Cited

U.S. PATENT DOCUMENTS

| | | | |
|---|---|---|---|
| 3,296,795 | 1/1967 | Nielsen | 219/121 LR |
| 3,348,547 | 10/1967 | Kavanagh | 128/395 |
| 3,703,176 | 11/1972 | Vassiliadis et al. | 128/303.1 X |
| 3,858,577 | 1/1975 | Bass et al. | 128/398 X |
| 3,906,953 | 9/1975 | Wallace et al. | 128/303.1 |
| 3,994,288 | 11/1976 | Stumpf | 128/6 |
| 4,057,332 | 11/1977 | Brubaker et al. | 219/121 LR |
| 4,141,362 | 2/1979 | Wurster | 128/303.1 |
| 4,144,888 | 3/1979 | Malyshev et al. | 128/303.1 |
| 4,146,019 | 3/1979 | Bass et al. | 128/6 |
| 4,164,222 | 8/1979 | Prokhiov et al. | 128/303.1 |
| 4,207,874 | 6/1980 | Choy | 128/303.1 X |
| 4,211,229 | 7/1980 | Wurster | 128/303.1 |

FOREIGN PATENT DOCUMENTS

| | | | |
|---|---|---|---|
| 2827639 | 1/1979 | Fed. Rep. of Germany | 128/303.1 |
| 1184814 | 3/1970 | United Kingdom | 128/395 |
| 2046510 | 11/1980 | United Kingdom | 128/303.1 |

*Primary Examiner*—Lee S. Cohen
*Attorney, Agent, or Firm*—Michael A. Kaufman

[57] ABSTRACT

A microsurgical laser device for guiding a laser beam to a desired target. The device includes a laser head that is vertically oriented and which is supported by a base that contains the required electronics for the system. This laser head can be tilted in all directions so as to position the device for use. The laser head is coupled to an articulated delivery system that allows for the delivery system, including a colposcope or an operating microscope, to be raised, lowered, tilted, rotated, and focused onto the target.

The articulated connection from the laser head to the colposcope or operating microscope makes use of a minimum number of mirrors to redirect the laser beam at 90 degree angles along a direction perpendicular to the axis of the incident path. Each mirror is mounted on precision mounts that obviate the need for adjustments.

In one embodiment of the device the articulated system makes use of three mirrors to redirect the beam and one lens to provide a fixed laser spot size at the target. In another embodiment of the device, four mirrors are used and two lenses are employed in order to provide a variable laser spot size at the target.

5 Claims, 5 Drawing Figures

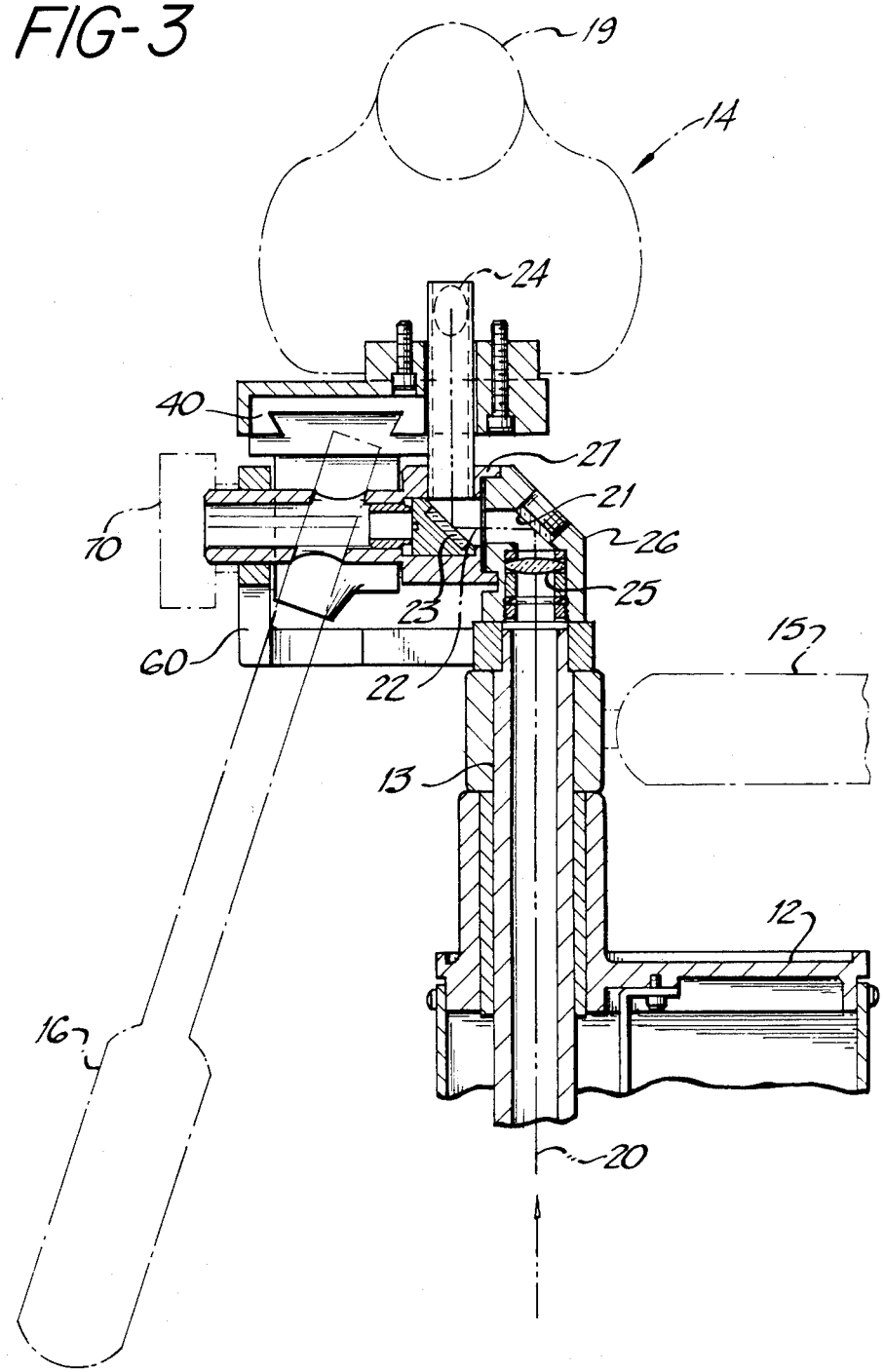

LASER DEVICE FOR GYNECOLOGY

TECHNICAL FIELD

The present invention relates to an apparatus for delivering a laser beam to tissues for the purpose of clinical intervention in the medical specialty of gynecology.

BACKGROUND ART

The development of the laser in 1960 opened the possibility of the application of this form of radiation in a number of medical disciplines. Lasers offered the advantages of high power, narrow spectral widths, small focused spot sizes, and good absorption of the energy by the target tissues.

Since then, numerous lasers of different wavelengths and modes of operation have been developed and many of these have been used in specific medical applications. For example, the argon laser, with emission in the blue-green part of the visible portion of the electromagnetic spectrum, has found extensive use in ophthalmology because of its good transmission by the ocular media and good absorption by the target tissues in the retina and choroid.

Among the many lasers that have been developed, however, the carbon dioxide laser, with its emission wavelength of 10.6 microns, offers the most extensive range of applications in medicine because it is highly absorbed by all tissues of the body. For this reason, by focusing the carbon dioxide laser on tissues it is possible to photocoagulate, to cut, or to vaporize almost any tissue of the body. The carbon dioxide laser has been applied to a number of medical problems in various disciplines - including otolaryngology, gynecology, neurology, and in general surgery.

The carbon dioxide laser has been used almost exclusively in the field of gynecology for medical intervention in a number of disorders. The laser is used for making incisions, to coagulate small arteries and veins, and to vaporize tumors and other abnormal tissues.

A number of instruments have been developed for use in the field of gynecology. These devices typically comprise a console that contains the power supplies, vacuum pump, gas tanks, and water pump and heat exchanger, for operating the laser. An umbilical cord is typically used to connect the console with a laser head that is directly coupled to a colposcope or an operating microscope, supported by a stand that is free standing or is connected to the console. These systems that have been developed have a number of disadvantages that make their clinical applications difficult. All such systems are somewhat awkward to use clinically because the laser is directly coupled to the microscope - thus any motion of the microscope also requires moving the whole laser head. In some systems, the laser head stand and the console comprise two large pieces of equipment that must be located near the patient resulting in space problems.

SUMMARY OF THE INVENTION

The present invention is directed to overcoming the disadvantages set forth above.

Accordingly, the present invention is designed to be a practical clinical device that is compact and easy to use. In contrast to previous devices, the subject device is in one unit in which the laser head housing doubles as the post on which the colposcope or operating microscope delivery system is attached.

In a preferred embodiment of the invention, the delivery system of the laser is mounted on a vertically oriented laser head housing that contains a carbon dioxide laser for treatment purposes, and a helium-neon laser that acts as an aiming beam, and a power monitor. The laser head is supported by a base that contains the power supplies, and other electronics necessary to operate the laser system. The laser beams are directed upward through an articulating system and delivered via an operating microscope or a colposcope that is supported by the laser head housing acting as a post. The housing can be tilted in any direction and thus provides one of the ways for positioning the operating microscope or colposcope for the delivery of the laser beams to the target areas.

The surgical carbon dioxide laser that is used in the system is sealed, r-f excited, and air cooled. This makes the present invention much simpler than prior systems that require water cooling and water pumps, a vacuum pump, and gas tanks. In addition, unlike other systems where the laser is operating continuously while the system is on, in this system the laser is off until a foot-switch is depressed and then the laser is turned on only for a preset duration or for as long as the foot-switch is depressed.

The subject apparatus incorporates a control panel that is conveniently located on the laser head housing that acts as a post. This panel contains the controls for adjusting laser power, time of exposure, and the on-off switches, and allows for the convenient setting of the required system characteristics by the operating physician.

BRIEF DESCRIPTION OF THE DRAWINGS

FIG. 3 is a cross-sectional view taken generally along line 3—3 of FIG. 2 of the delivery system showing the mirrors and lens that are used;

DESCRIPTION OF THE PREFERRED EMBODIMENT

Figure 1:
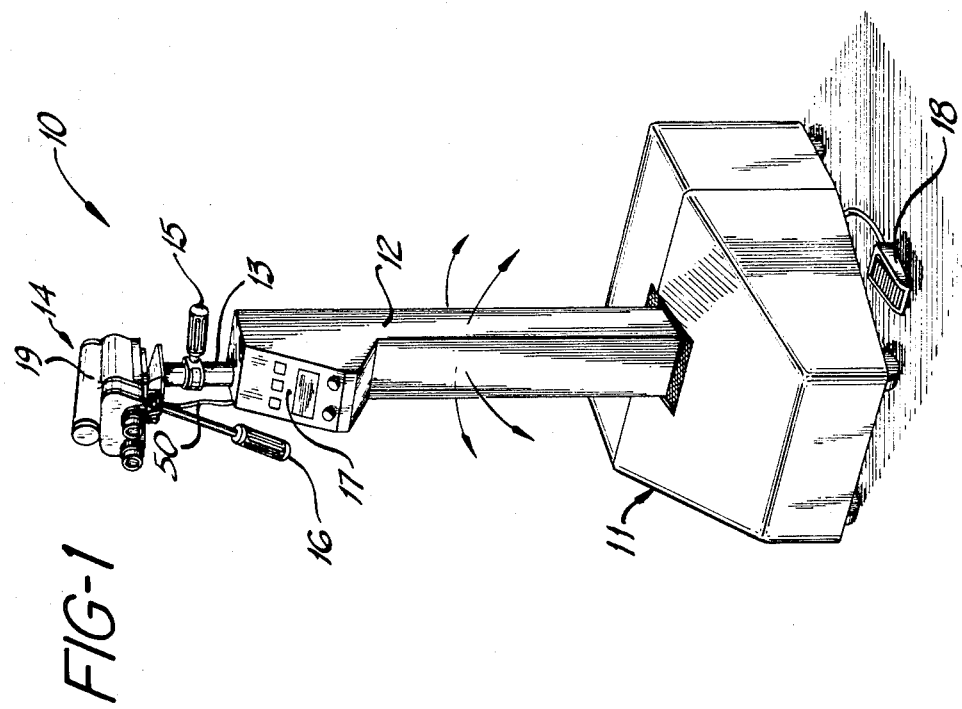
FIG. 1 is an overall perspective view of an illustrative laser device for gynecology according to the invention including a base, a laser head acting as a post, a control panel, and a colposcope or operating microscope delivery system.

FIG. 1 shows an overall schematic view of the present invention, a microsurgical laser device for gynecology generally referred to as 10. The laser device 10 comprises a mobile base 11 that houses necessary power supplies and required electronics. A generally vertical laser head housing 12 is hinge supported by the base 11 and functions as a post for a small telescoping support 13 that in turn supports a colposcope or operating microscope delivery system referred to generally as 14.

The laser head housing 12 contains a carbon dioxide laser that is used for treatment, such as a Laakmann ElectroOptics, Inc. rf excited carbon dioxide waveguide laser, and a helium-neon laser used for aiming purposes since the beam of the carbon dioxide laser is invisible to the eye. The beams of the two lasers are combined by a method well known to those familiar with the art, and are directed upward into the telescoping support 13 that is hollow so that the beams can propagate along its central or longitudinal axis. The laser head housing 12 is designed to pivot within the base 11 and it can be tilted in any direction about the vertical; thus, allowing for the approximate aiming of the delivery system 14 onto the target site.

The colposcope or operating microscope delivery system 14 can be more accurately positioned and focused by adjustment of control handles 15 and 16. The colposcope is mounted on support 13 by means of a carriage 60. The laser beam is delivered via colposcope or microscope viewing head 19 by redirecting the beams along rotational axes using three or more mirrors depending on the particular colposcope that is used. The laser device is controlled by the use of a control panel 17 that has provisions for switching the carbon dioxide and helium-neon lasers on or off, for adjusting the power level of the carbon dioxide laser, and for setting the length of time the carbon dioxide laser will be on when a footswitch 18 is activated by the operating physician.

Figure 2:
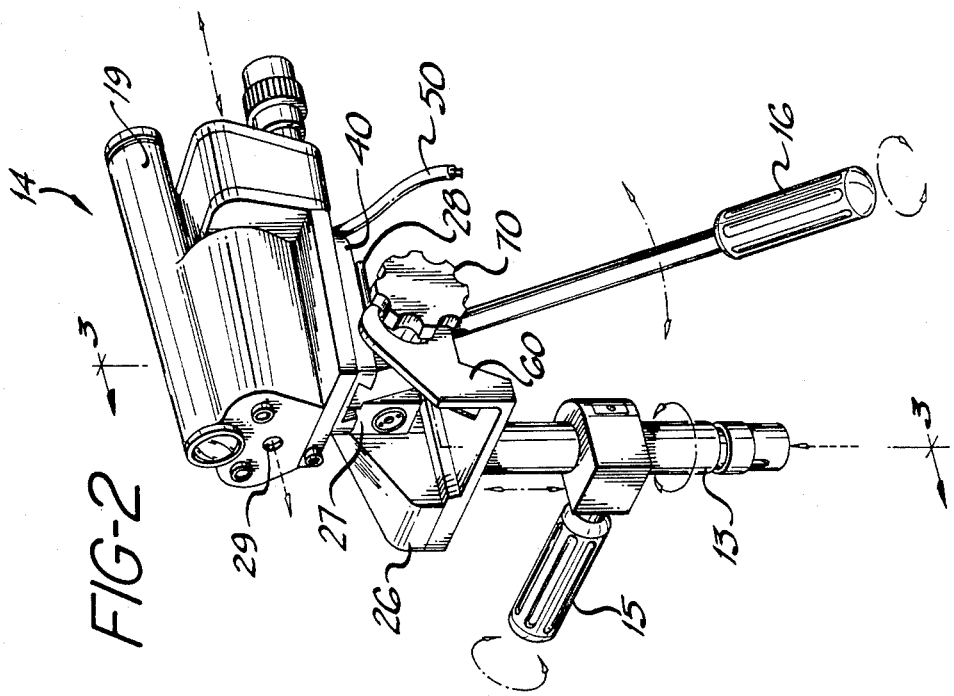
FIG. 2 is an enlarged perspective view of the colposcope or operating microscope delivery system.

The delivery system is shown in greater detail in FIG. 2. The support 13 is rotatable about its axis by the use of a first multiple function control handle 15. The height of support 13 is altered to thereby raise or lower the operating microscope 14 by rotation of the handle 15 about its axis. The colposcope or microscope 14 may be tilted up or down from the horizontal position by pivoting a second multiple function control handle 16. In addition, the colposcope or microscope viewing head 19 is moved toward or away from the target in order to focus the device by rotation of the handle 16 about its axis. Thus, the colposcope or microscope delivery system is adapted to be accurately positioned and to be pointed optimally for the delivery of the laser beams to the target sites.

The operation of the laser device for gynecology is as follows:

With the patient in position on an examining table (not shown), the laser device 10 is wheeled into position and the laser head housing 12 is tilted in an appropriate position to bring it into the proximity of the required operating position. The lasers contained in housing 12 are switched on by the controls on the control panel 17, the power is adjusted to the desired level, and the time of exposure is set to a specific value, or it is set for continuous operation. A cable 50 is provided to furnish light to the colposcope or operating microscope. For all settings, the foot-switch 18 is the control for initiating the exposure and at all times for terminating the exposure unless exposure is terminated automatically at the preset value. The laser is brought to the target site by proper manipulation of the handles 15 and 16. Treatment is carried out by the application of the carbon dioxide laser exposures using the foot-switch 18.

The articulated delivery system that is used to deliver the laser beams to the target site is shown partially schematically in FIG. 3. The optical path that is used includes three mirrors to redirect the beams along the mechanical axes of the delivery system. Referring now to FIG. 3 the carbon dioxide laser and the helium-neon laser beams, are combined in the laser head 12 and the colinear laser beams are directed upward along a first axis 20 that is the longitudinal axis of the telescoping support 13. The support is rotatable about the axis 20 by the use of the handle 15. In addition, the support 13 can be raised or lowered by rotating the handle 15 about its axis. In this way, the colposcope or operating microscope 14 that is used to view and direct the laser beams onto the target may be properly positioned in height.

The laser beams proceed upward and are reflected at 90 degrees by the first redirecting means such as precision mounted mirror 21 along a second axis 22, orthogonal to the first. This axis of rotation provides the system with the freedom to tilt the colposcope or operating microscope 14 up or down. This is accomplished by pivoting the handle 16. In addition, by rotating the handle 16 about its axis, as shown in greater detail in FIG. 4, the delivery system 14, including the colposcope or operating microscope viewing head 19 can be moved toward or away from the target site so as to focus the device. The laser beams are then reflected by a second redirecting means such as precision mounted mirror 23 upward into the colposcope or operating microscope viewing head 19. The beams are then reflected from a third redirecting means such as adjustable mirror 24 in a forward direction toward the target. This last mirror 24 can be manipulated via mechanical means well known to those familiar with the art, preferably such as by connecting it to a joy-stick that permits the operating physician to freely move the laser beams to targets of interest within the field of view of the colposcope or microscope.

The configuration that has been shown in FIG. 3 makes use of the minimum number of mirrors and still provides the delivery system with all of the degrees of freedom required to easily manipulate the colposcope and the laser beams within the range of targets of interest to the physician.

Referring again to FIG. 3, it is noted that the laser beams pass through a focusing lens 25 on their path through the delivery system to the target site. The focal length and location of the lens are selected so as to give a specific and useful spot size for the carbon dioxide laser at the focal plane of the viewing optics of the colposcope or operating microscope 14. This selection of lens characteristics and location are easily made by those familiar with the art.

Figure 4:
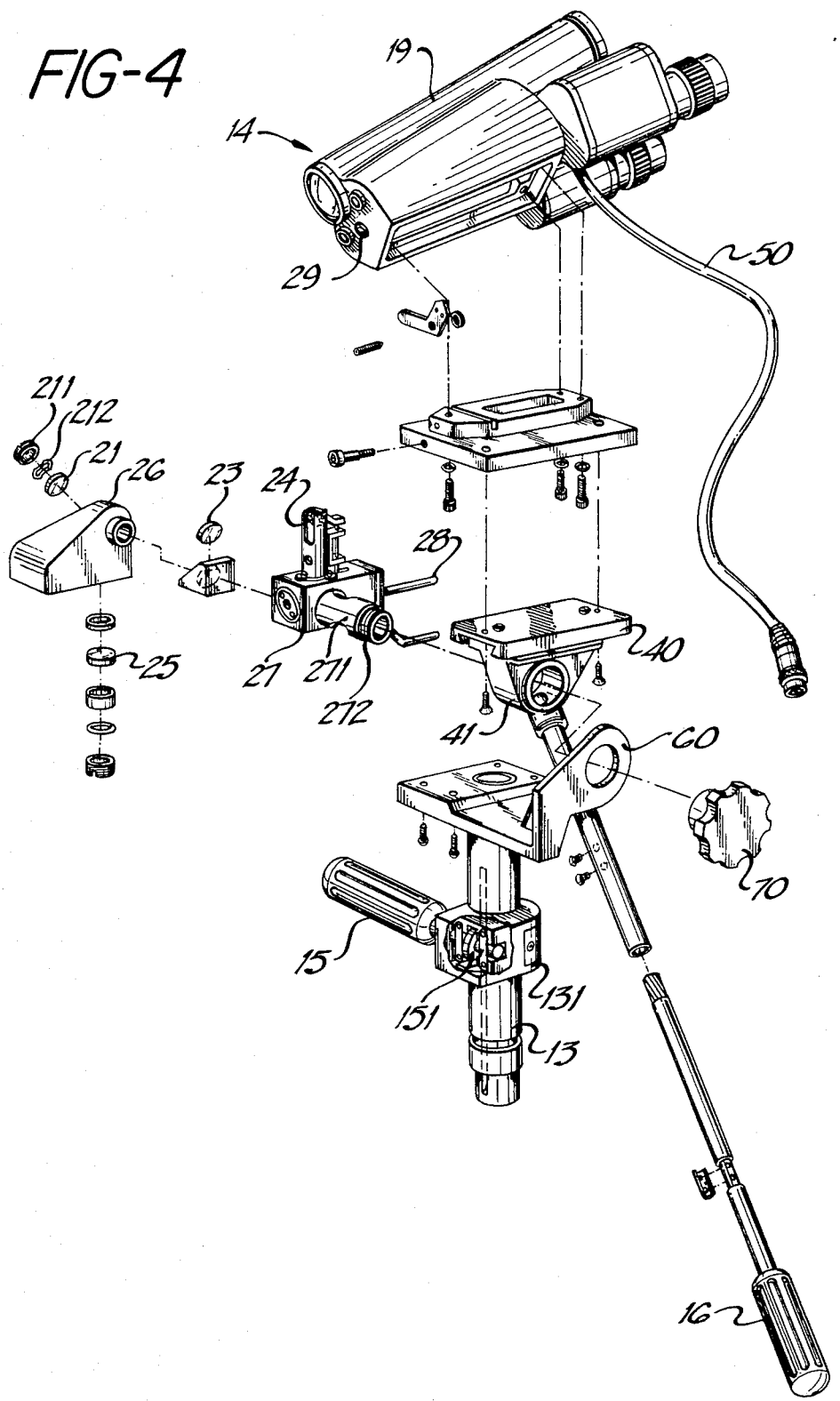
FIG. 4 is an exploded view of the delivery system showing the coupling from the laser head to the colposcope or the operating microscope.

This embodiment of the delivery system is also shown in FIG. 4 which presents an exploded view of the three-mirror coupling to the colposcope or operating microscope 14. Referring to FIG. 4, the combined laser beams enter the telescopic support 13 along its axis from the laser head. This support may be moved up or down by the rotation of handle 15 which rotates a wheel 151 enclosed within collar 131 of the support 13. The beams then pass through the focusing lens 25 that is housed in a block 26. Also housed in block 26 is the first mirror 21 that redirects the laser beams along axis 22. Mirror 21 is precision mounted within block 26 by means of threaded annular retaining member 211 and resilient means such as O-ring 212. The beams then enter block 27 and are reflected upward by second mirror 23 (also precision mounted) onto the third mirror 24 that redirects the beam forward and out of the colposcope 14. Block 27 also contains the mechanical linkages that allow the mirror 24 to be manipulated freely by the joy-stick 28 so that the combined beams are directed to the target. Cylindrical member 271 of block 27 is configured to fit within collar 41 and its threaded end portion 272 is matingly engaged by knob 70. The laser beams exit the colposcope or operating microscope 14 through an aperture 29 on their path to the targets.

Rotation of second handle 16 about its axis causes base plate 40 to be translated thereby resulting in the colposcope viewing head 19 mounted thereon being moved toward or away from the target depending on whether the rotation is clockwise or counterclockwise.

The embodiment of the delivery system described above and depicted in FIGS. 2-4 represents the simplest useful configuration that can be used for gynecological applications. This system provides a carbon dioxide laser spot size at the target site that is of a practical value, such as 1.5 mm in diameter. Although this provides a useful device for performing various procedures of interest to the gynecologist, there are situations where it is advantageous to provide a means for varying the diameter of the laser spot size produced at the target. Thus, a variation of the spot diameter over a range from 500 microns to 2000 microns, for example, would provide the physician with additional flexibility in the delivery of energy to the tissues.

Figure 5:
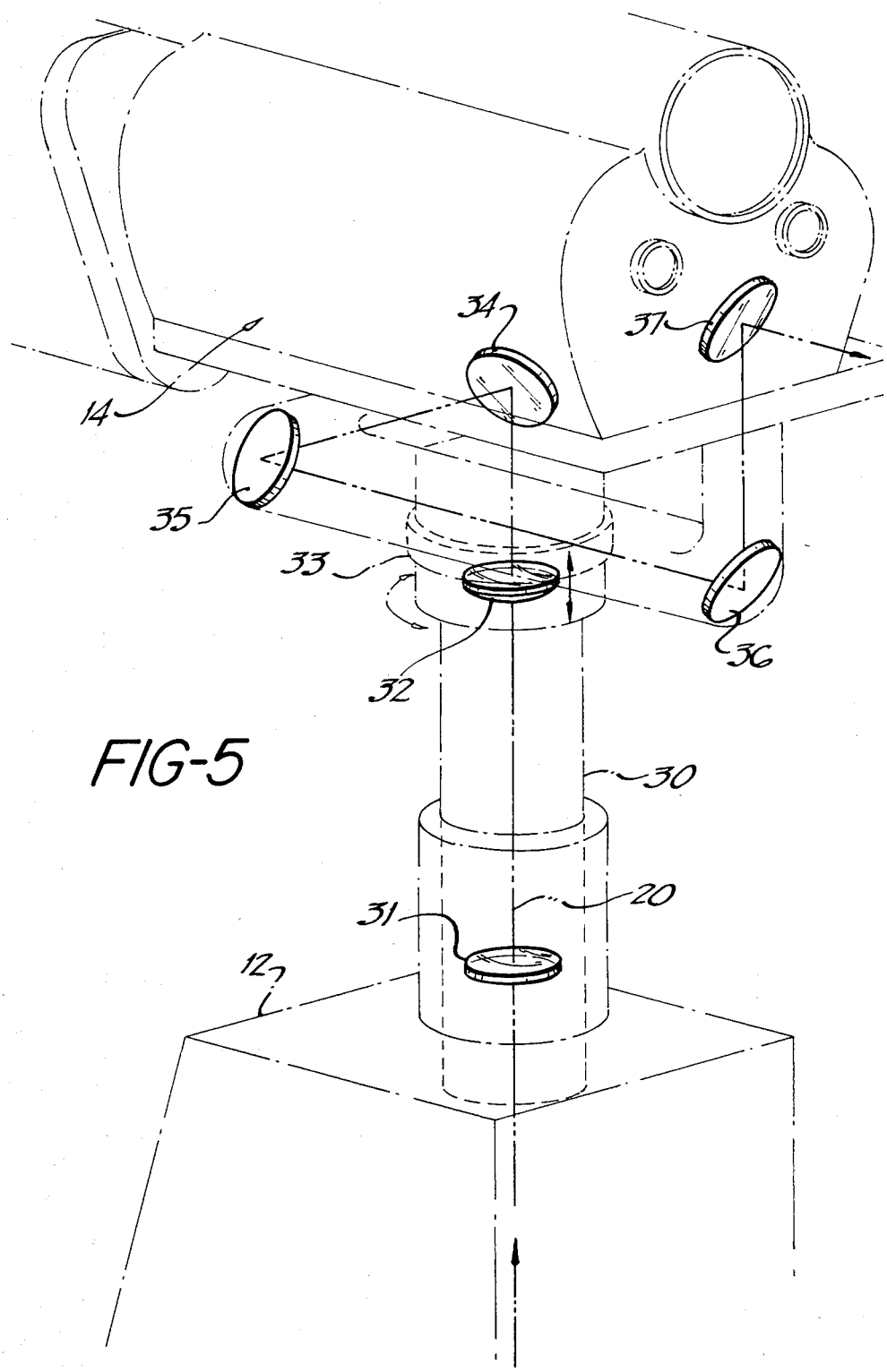
FIG. 5 is a schematic view of an alternate embodiment of the delivery system that provides for a variable spot size of the laser beam at the target site.

An embodiment that provides the variation of spot size of the laser beams at the target is schematically shown in FIG. 5. Referring now to FIG. 5, a carbon dioxide laser and a helium-neon laser are contained in the laser head housing 12 and their beams are combined such that they enter the post 30 coaxially along the axis 20 of the post 30. The beams pass through two lenses 31 and 32 on their path to the target. The first lens 31 is fixed and is a concave lens that diverges the laser beams while lens 32 is a convex lens that focuses the laser beams. This second lens 32 is movable by means of a dial 33 so that its distance from the first lens 31 is varied. In this way the size of the carbon dioxide laser beam at the target site can be varied over a range of values. The focal lengths and locations of the lenses can be easily selected by those familiar with the art so as to provide the spot size variation that is required. After passing through the lenses 31 and 32 the laser beams are redirected by means of four mirrors 34, 35, 36, and 37. These mirrors reflect the laser beams along axes that are perpendicular to each other thus providing the colposcope or operating microscope 14 with the degrees of freedom necessary to easily position and manipulate the device. The last mirror 37 is preferably linked mechanically to a joy-stick by methods well known to those familiar with the art, so as to allow free control of the target site to the operating physician. Beam motion with the joy-stick could also be accomplished by mechanical linkage to one of the other mirrors such as 36 or 35, for example.

I claim:

1. A self-contained surgical laser system for delivering laser energy to selected target sites to vaporize tissue such as in gynecological applications which comprises:
    (a) a generally vertical column housing a $CO_2$ laser for emitting a first laser beam, a second laser of the type emitting a laser beam visible to the unaided human eye and means for optically aligning said laser beams;
    (b) a stable movable base member pivotally anchoring said column, said base member including means for permitting said column to be universally pivoted relative to an axis intersecting said base member;
    (c) a hollow telescopic support member supported by said column and positioned for transmitting said laser beams therethrough;
    (d) means connected to said telescopic member for tilting said column relative to the location of the desired target site; and
    (e) viewing means supported by said telescopic support member for aiming, microscopically viewing and delivering said laser beams from said support member to a desired target site without moving either said vertical column or said base member.

2. The laser system apparatus according to claim 1 wherein said viewing means includes means for tilting said viewing means relative to said telescopic support member.

3. The laser system apparatus according to claim 2 wherein said viewing means further comprises means for rotating said viewing means about a vertical axis passing through said hollow telescopic support member.

4. The laser system apparatus according to claim 3 wherein said viewing means further comprises means for translating said viewing means along a line intersecting the desired target site.

5. The laser system apparatus according to claim 2 wherein said viewing means further comprises means for translating said viewing means along a line intersecting the desired target site.

* * * * *